(12) United States Patent
Blood et al.

(10) Patent No.: US 6,794,489 B2
(45) Date of Patent: Sep. 21, 2004

(54) COMPOSITIONS AND METHODS FOR TREATMENT OF SEXUAL DYSFUNCTION

(75) Inventors: Christine H. Blood, Morristown, NJ (US); Annette M. Shadiack, Sommerset, NJ (US); Joanna K. Bernstein, North Brunswick, NJ (US); Guy H. Herbert, Metuchen, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 136 days.

(21) Appl. No.: 10/040,547

(22) Filed: Jan. 4, 2002

(65) Prior Publication Data

US 2002/0107182 A1 Aug. 8, 2002

Related U.S. Application Data

(63) Continuation-in-part of application No. 09/606,501, filed on Jun. 28, 2000, now Pat. No. 6,579,968.
(60) Provisional application No. 60/142,346, filed on Jun. 29, 1999, and provisional application No. 60/194,987, filed on Apr. 5, 2000.

(51) Int. Cl.$^7$ .................. A61K 38/00; A61K 38/12; C07K 7/00; C07K 7/64
(52) U.S. Cl. .................. 530/312; 530/317; 530/321; 530/300; 530/328; 530/329; 514/9; 514/11; 514/12; 514/15; 514/16; 514/18; 424/9.1; 436/811
(58) Field of Search .................. 530/312, 317, 530/321, 300, 328, 329; 514/9, 11, 12, 15, 16, 18; 424/9.1; 436/811

(56) References Cited

U.S. PATENT DOCUMENTS

| | | | |
|---|---|---|---|
| 3,853,836 A | * | 12/1974 | Greven et al. ............ 260/112.5 |
| 3,862,928 A | * | 1/1975 | De Wied et al. .......... 260/112.5 |
| 4,649,191 A | * | 3/1987 | Hruby et al. ................ 530/329 |
| 5,420,109 A | | 5/1995 | Suto et al. |
| 5,576,290 A | | 11/1996 | Hadley |
| 5,674,839 A | | 10/1997 | Hruby et al. |
| 5,693,608 A | | 12/1997 | Bechgaard et al. |
| 5,714,576 A | | 2/1998 | Hruby et al. |
| 5,908,825 A | | 6/1999 | Fasano et al. |
| 5,977,070 A | | 11/1999 | Piazza et al. |
| 6,051,555 A | | 4/2000 | Hadley |
| 6,054,556 A | | 4/2000 | Hruby et al. |
| 6,579,968 B1 | * | 6/2003 | Blood et al. ................ 530/312 |

FOREIGN PATENT DOCUMENTS

| FR | 2 691 465 | 11/1993 |
|---|---|---|
| FR | 2 735 131 | 12/1996 |
| WO | WO 94/22460 | 10/1994 |

OTHER PUBLICATIONS

Bednarek M.A. et al., "Structure–function studies onthe cyclic peptide MT–II, lactam derivative of α–melanotropin," *Peptides*, vol. 20:401–09 (1999).
Hadley M.E. et al., "Melanocortin Receptors: Identification and Characterization by Melantropic Peptide Agonists and Antagonists," *Pigment Cell Res*, vol. 9:213–34 (1996).
Haskell–Luevano C. et al., "Discovery of Prototype Peptidomimetic Agonists at the Human Melanocortin Receptors MC1R and MC4R," *Journal of Medical Chemistry*, vol. 40:2133–39 (1997).
Hruby, V.J., et al., "Cyclic Lactam α–melanocyte–stimulating Hormone–(4–10)–NH$_2$ with bulky aromatic amino acids at position 7 show high antagonist potency and selectivity at specific melanocortin receptors, " *Journal of Medicinal Chemistry*, vol. 38, No. 18: 3454–61 (1995).
Schiöth H.B. et al., "Discovery of novel melanocortin$_4$ receptor selective MSH analogues," *British Journal of Pharmacology*, vol. 124:75–82 (1998).
Schiöth H.B. et al., "Selective properties of C– and N–terminals and core residues of the melanocyte–stimulating hormone on binding to the human melanocortin receptor subtypes," *European Journal of Pharmacology*, vol. 349:359–66 (1998).
Wessells H. et al., "Synthetic Melanotropic peptide initiates erections in men with psychogenic erectile dysfunction: double–blind, placebo controlled crossover study," *Journal of Urology*, vol. 160:389–393 (1998).
Low, et al., "Role of Chain Termini in Selective Steroidogenic Effect of ACTH MSh–4–10 on Isolated Adrenocortical Cells," Peptides (Elmsford), vol. 11, No. 1, 1990, pp. 29–32.
"Synthesis and Receptor Binding Analysis of Thirteen Oligomeric *–MSH Analogs," Brandenburger, Yves, et al., J. of Receptor & Signal Transduction Research, vol. 19, No. 1–4, 1999, pp. 467–480.
Chemical Abstracts, Chemical Substance Index, Part 5 of 9, Chemical Abstracts Service, vol. 126, Jun. 30, 1997, pp. 9239CS and 9257CS.

* cited by examiner

Primary Examiner—Christopher S. F. Low
Assistant Examiner—Chih-Min Kam
(74) Attorney, Agent, or Firm—Stephen A. Slusher; Peacock, Myers&Adams, P.C.

(57) ABSTRACT

Compositions and methods are provided for treatment of sexual dysfunction in mammals, including male sexual dysfunction, such as erectile dysfunction, and female sexual dysfunction. In one embodiment, a peptide-based composition including the peptide sequence Ac-Nle-cyclo(-Asp-His-D-Phe-Arg-Trp-Lys)-OH is administered. Methods of administration include injection, oral, nasal and mucosal administration.

18 Claims, 8 Drawing Sheets

COMPOSITIONS AND METHODS FOR TREATMENT OF SEXUAL DYSFUNCTION

CROSS-REFERENCE TO RELATED APPLICATIONS

This application is a continuation-in-part application of U.S. patent application Ser. No. 09/606,501, now U.S. Pat. No. 6,579,968, entitled *Compositions And Methods For Treatment Of Sexual Dysfunction*, filed on Jun. 28, 2000, and the specification thereof is incorporated herein by reference. This application further claims the benefit of the filing of U.S. Provisional Patent Application Serial No. 60/142,346, entitled *Compositions And Methods For Treatment Of Sexual Dysfunction*, filed on Jun. 29, 1999, and U.S. Provisional Patent Application Serial No. 60/194,987, entitled *Compositions And Nasal Deliver Methods For Treatment Of Sexual Dysfunction*, filed on Apr. 5, 2000, and the specification thereof of each is incorporated herein by reference.

BACKGROUND OF THE INVENTION

1. Field of the Invention (Technical Field)

The present invention relates to peptide constructs for the treatment of sexual dysfunction in animals, including both male erectile dysfunction and female sexual dysfunction, including methods and formulations for the use and administration of the same.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Sexual dysfunction, including both penile erectile dysfunction or impotence and female sexual dysfunction, are common medical problems. Significant effort has been devoted over the last twenty or more years to develop methods, devices and compounds for treatment of sexual dysfunction. While more effort has been undertaken for treatment of penile erectile dysfunction, female sexual dysfunction is also an area to which significant research and effort has been devoted.

At present, one commonly used orally administered drug for treatment of sexual dysfunction in the male is Viagra®, a brand of sildenafil, which is a phosphodiesterase 5 inhibitor, increasing the persistence of cyclic guanosine monophosphate and thereby enhancing erectile response. There are several other medical treatment alternatives currently available depending on the nature and cause of the impotence problem. Some men have abnormally low levels of the male hormone testosterone, and treatment with testosterone injections or pills may be beneficial. However, comparatively few impotent men have low testosterone levels. For many forms of erectile dysfunction, treatment may be undertaken with drugs injected directly into the penis, including drugs such as papaverin, prostaglandin $E_1$, phenoxybenzamine or phentolamine. These all work primarily by dilating the arterial blood vessels and decreasing the venous drainage. Urethral inserts, such as with suppositories containing prostaglandin, may also be employed. In addition, a variety of mechanical aids are employed, including constriction devices and penile implants.

A variety of treatments have also been explored for female sexual dysfunction, including use of sildenafil, although the Food and Drug Administration has not specifically approved such use. Testosterone propionate has also been employed to increase or augment female libido.

Melanocortin receptor-specific compounds have been explored for use of treatment of sexual dysfunction. In one report, a cyclic α-melanocyte-stimulating hormone ("α-MSH") analog, called Melanotan-II, was evaluated for erectogenic properties for treatment of men with psychogenic erectile dysfunction. Wessells H. et al., *J Urology* 160:389–393 (1998); see also U.S. Pat. No. 5,576,290, issued Nov. 19, 1996 to M. E. Hadley, entitled *Compositions and Methods for the Diagnosis and Treatment of Psychogenic Erectile Dysfunction* and U.S. Pat. No. 6,051,555, issued Apr. 18, 2000, also to M. E. Hadley, entitled *Stimulating Sexual Response in Females*. The peptides used in U.S. Pat. Nos. 5,576,290 and 6,051,555 are also described in U.S. Pat. No. 5,674,839, issued Oct. 7, 1997, to V. J. Hruby, M. E. Hadley and F. Al-Obeidi, entitled *Cyclic Analogs of Alpha-MSH Fragments*, and in U.S. Pat. No. 5,714,576, issued Feb. 3, 1998, to V. J. Hruby, M. E. Hadley and F. Al-Obeidi, entitled *Linear Analogs of Alpha-MSH Fragments*. Melanotan-II is a peptide of the following formula:

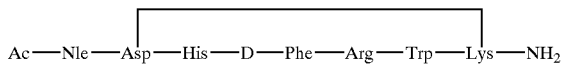

Additional related peptides are disclosed in U.S. Pat. Nos. 5,576,290, 5,674,839, 5,714,576 and 6,051,555. These peptides are described as being useful for both the diagnosis and treatment of psychogenic sexual dysfunction in males and females. These peptides are related to the structure of melanocortins.

In use of Melanotan-II, significant erectile responses were observed, with 8 of 10 treated men developing clinically apparent erections, and with a mean duration of tip rigidity greater than 80% for 38 minutes with Melanotan-II compared to 3.0 minutes with a placebo (p=0.0045). The drug was administered by subcutaneous abdominal wall injection, at doses ranging from 0.025 to 0.157 mg/kg body weight. Transient side effects were observed, including nausea, stretching and yawning, and decreased appetite.

The minimum peptide fragment of native α-MSH needed for erectile response is the central tetrapeptide sequence, $His^6$-$Phe^7$-$Arg^8$-$Trp^9$ (SEQ ID NO:1). In general, all melanocortin peptides share the same active core sequence, His-Phe-Arg-Trp (SEQ ID NO:1), including melanotropin neuropeptides and adrenocorticotropin. Five distinct melanocortin receptor subtypes have been identified, called MC1-R through MC5-R, and of these MC3-R and MC4-R are believed to be expressed in the human brain. MC3-R has the highest expression in the arcuate nucleus of the hypothalamus, while MC4-R is more widely expressed in the thalamus, hypothalamus and hippocampus. A central nervous system mechanism for melanocortins in the induction of penile erection has been suggested by experiments demonstrating penile erection resulting from central intracerebroventricular administration of melanocortins in rats. While the mechanism of His-Phe-Arg-Trp (SEQ ID NO:1) induction of erectile response has not been fully elucidated, it has been hypothesized that it involves the central nervous system, and probably binding to MC3-R and/or MC4-R.

Other peptides and constructs have been proposed which are ligands that alter or regulate the activity of one or more melanocortin receptors. For example, International Patent Application No. PCT/US99/09216, entitled *Isoquinoline Compound Melanocortin Receptor Ligands and Methods of Using Same*, discloses two compounds that induce penile erections in rats. However, these compounds were administered by injection at doses of 1.8 mg/kg and 3.6 mg/kg, respectively, and at least one compound resulted in observable side effects, including yawning and stretching. Other melanocortin receptor-specific compounds with claimed application for treatment of sexual dysfunction are disclosed in International Patent Application No. PCT/US99/13252, entitled *Spiropiperidine Derivatives as Melanocortin Receptor Agonists*.

Both cyclic and linear α-MSH peptides have been studied; however, the peptides heretofore evaluated have had an amide or —$NH_2$ group at the carboxyl terminus. See, for example, Wessells H. et al., *J Urology*, cited above; Haskell-Luevano C. et al., *J Med Chem* 40:2133–39 (1997); Schiöth H. B. et al., *Brit J Pharmacol* 124:75–82 (1998); Schiöth H. B. et al., *Eur J Pharmacol* 349:359–66 (1998); Hadley M. E. et al., *Pigment Cell Res* 9:213–34 (1996); Bednarek M. A. et al., *Peptides* 20:401–09 (1999); U.S. Pat. Nos. 6,054,556, 6,051,555 and 5,576,290; and, International Patent Applications PCT/US99/04111 and PCT/US98/03298. While significant research has been conducted in an effort to determine the optimal structure of α-MSH peptides, including a variety of structure-function, agonist-antagonist, molecular modeling and pharmacophore studies, such studies have relied upon peptides with an art conventional —$NH_2$ group at the carboxyl terminus. Further, it has long been believed that biologically active neuropeptides, including α-MSH peptides, are amidated, with an —$NH_2$ group at the carboxyl terminus, and that such amidation is required both for biological activity and stability. See, for example, *Metabolism of Brain Peptides*, Ed. G. O'Cuinn, CRC Press, New York, 1995, pp. 1–9 and 99–101.

SUMMARY OF THE INVENTION
(DISCLOSURE OF THE INVENTION)

The invention relates to a peptide that is a free acid or pharmaceutically acceptable salt thereof that includes the sequence His-Phe-Arg-Trp (SEQ ID NO:1), His-D-Phe-Arg-Trp, homologs of His-Phe-Arg-Trp (SEQ ID NO:1) or homologs of His-D-Phe-Arg-Trp. The peptide is preferably a cyclic peptide, and preferable has a terminal —OH at the carboxyl terminus. In a preferred embodiment, the peptide is Ac-Nle-cyclo(-Asp-His-D-Phe-Arg-Trp-Lys)-OH.

The invention also includes pharmaceutical compositions of matter, including a peptide of this invention and a pharmaceutically acceptable carrier. The pharmaceutically acceptable carrier may be a buffered aqueous carrier, and preferably a saline or citrate buffered carrier.

The peptide of this invention, and pharmaceutical compositions of this invention, may be used for stimulating sexual response in a mammal. The invention thus also includes a method for stimulating sexual response in a mammal, in which a pharmaceutically sufficient amount of a composition including His-Phe-Arg-Trp (SEQ ID NO:1), His-D-Phe-Arg-Trp, homologs of His-Phe-Arg-Trp (SEQ ID NO:1) or homologs of His-D-Phe-Arg-Trp is administered. In a preferred embodiment, the composition includes a peptide or pharmaceutically acceptable salt thereof of the formula Ac-Nle-cyclo(-Asp-His-D-Phe-Arg-Trp-Lys)-OH. The mammal may be male or female. In this method, the composition can also include a pharmaceutically acceptable carrier. The peptide or pharmaceutical composition may be administered by any means known in the art, including administration by injection, administration through mucous membranes, buccal administration, oral administration, dermal administration, inhalation administration and nasal administration. In a preferred embodiment, administration is by nasal administration of a metered amount of a formulation including an aqueous buffer, which buffer may be a saline or citrate buffer.

A primary object of the present invention is a melanocortin receptor-specific pharmaceutical for use in treatment of sexual dysfunction.

A second object is to provide a peptide-based melanocortin receptor-specific pharmaceutical for use in treatment of male sexual dysfunction, including erectile dysfunction.

Yet another object is to provide a peptide-based melanocortin receptor-specific pharmaceutical for use in treatment of female sexual dysfunction.

Yet another object is to provide a peptide-based melanocortin receptor-specific pharmaceutical for use in treatment of sexual dysfunction with substantially reduced incidence of undesirable side effects.

A primary advantage of the present invention is that it is efficacious at doses that do not cause deleterious side effects, such side effects including nausea, yawning, stretching, decreased appetite and other effects observed with Melanotan-II, or that causes decreased deleterious side effects as compared to Melanotan-II.

A second advantage of the present invention is that it provides compositions with a larger therapeutic window between desired therapeutic effects and the onset of undesired side effects than other melanocortin receptor-specific agents for the intended purpose.

Yet another advantage of the present invention is that it provides compositions with a greater safety margin between desired therapeutic effects and the onset of undesired side effects than other melanocortin receptor-specific agents for the intended purpose.

Yet another advantage of the present invention is that it provides a peptide-based melanocortin receptor-specific pharmaceutical for use in treatment of sexual dysfunction which is efficacious at significantly lower doses than Melanotan-II or other melanocortin receptor-specific agents.

Yet another advantage of the present invention is that it provides a peptide-based melanocortin receptor-specific pharmaceutical that is effective over a greater dose range, without deleterious side effects, than Melnotan-II or other melanocortin receptor-specific agents.

Yet another advantage of the present invention is that it provides a peptide-based melanocortin receptor-specific pharmaceutical for use in treatment of sexual dysfunction which is pharmaceutically active more rapidly following administration than Melanotan-II or other peptide-based melanocortin receptor-specific agents.

Yet another advantage of the present invention is that it provides a peptide-based melanocortin receptor-specific pharmaceutical for use in treatment of sexual dysfunction which, because of increased efficacy at low doses, may be administered by delivery systems other than art conventional intravenous, subcutaneous or intramuscular injection, including but not limited to nasal delivery systems and mucous membrane delivery systems.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

Figure 1:
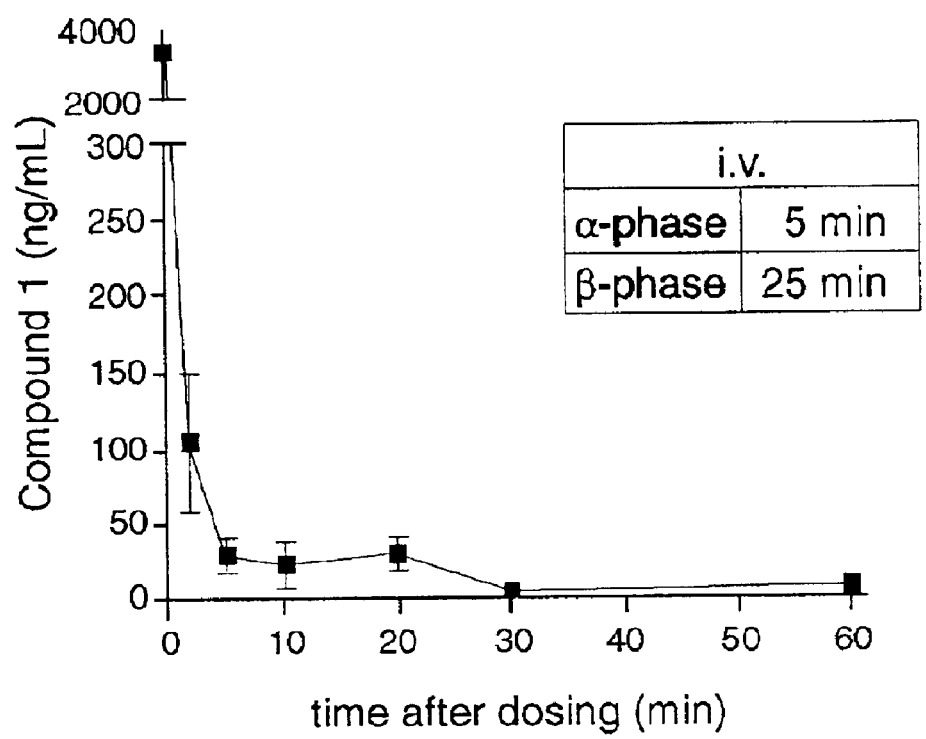
FIG. 1 is a plot of the pharmacokinetic profile in rats intravenously administered 100 μg/kg body weight of Compound 1.

DESCRIPTION OF THE PREFERRED EMBODIMENTS (BEST MODES FOR CARRYING OUT THE INVENTION)

In the listing of compounds according to the present invention, the amino acid residues have their conventional meaning as given in Chapter 2400 of the *Manual of Patent Examining Procedure*, 7th Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine, and "Ser" is serine. "Ac" refers to a peptide or amino acid sequence that is acetylated.

The invention provides deamidated α-MSH peptides, which are peptides that include the core α-MSH sequence His-Phe-Arg-Trp (SEQ ID NO:1), His-D-Phe-Arg-Trp, or homologs or analogs of either of the foregoing, in which the peptide is deamidated, which is to say that it does not include an —$NH_2$ group at the carboxyl terminus. In a preferred embodiment, the deamidated α-MSH peptides of this invention have an —OH group at the carboxyl terminus, and are thus a free acid form of peptide.

In a preferred embodiment, the invention provides the peptide

Ac-Nle-cyclo(-Asp-His-D-Phe-Arg-Trp-Lys)-OH    Compound 1

The peptide of Compound 1 has a formula of $C_{50}H_{68}N_{14}O_{10}$, and a net molecular weight of 1025.18. This peptide may be synthesized by solid-phase means and purified to greater than 96% purity by HPLC, yielding a white powder that is a clear, colorless solution in water. The structure of Compound 1 is:

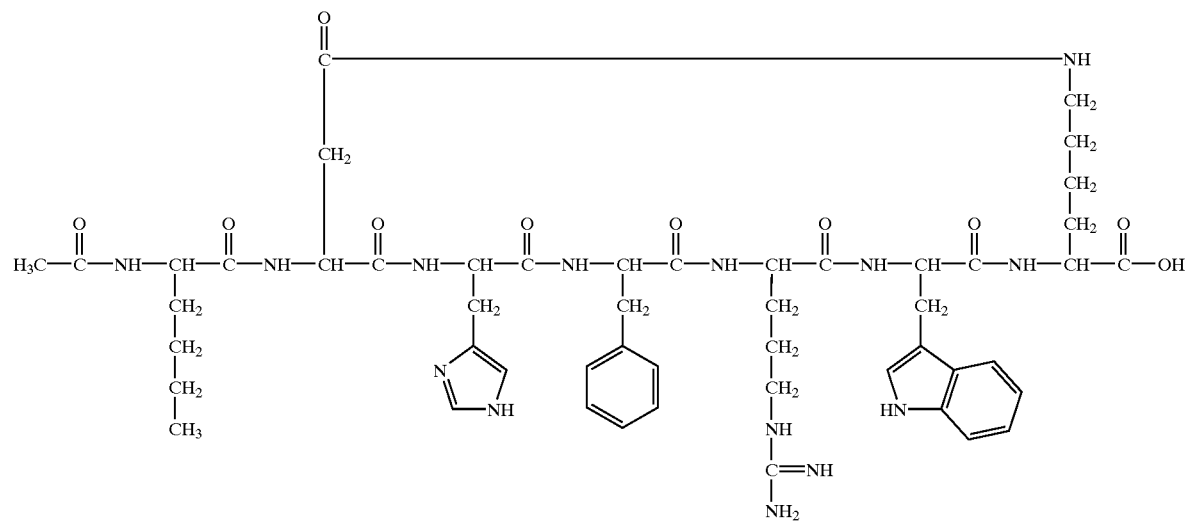

In general, the peptide compounds of this invention may be synthesized by solid-phase synthesis and purified according to methods known in the art. Any of a number of well-known procedures utilizing a variety of resins and reagents may be used to prepare the compounds of this invention.

The peptides of this invention may be in the form of any pharmaceutically acceptable salt. Acid addition salts of the compounds of this invention are prepared in a suitable solvent from the peptide and an excess of an acid, such as hydrochloric, hydrobromic, sulfuric, phosphoric, acetic, trifluoroacetic, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The invention provides a pharmaceutical composition that includes a peptide of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

Routes of Administration.

Because, in part, of the increased potency of Compound 1 and the other peptides of this invention, these peptides may be administered by means other than by injection. If it is administered by injection, the injection may be intravenous, subcutaneous, intramuscular, intraperitoneal or other means known in the art. The peptides of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may include administration through mucous membranes, buccal administration, oral administration, dermal administration, inhalation administration, nasal administration and the like. The dosage for treatment of male erectile dysfunction is administration, by any of the foregoing means or any other means known in the art, of an amount sufficient to bring about an erection of the penis in a male. The dosage for treatment of female sexual dysfunction is administration, by any of the foregoing means or any other means known in the art, of an amount sufficient to bring about the desired response.

The peptides of this invention may be formulated or compounded into pharmaceutical compositions that include at least one peptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride or sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of this invention over a period of time.

In general, the actual quantity of peptides of this invention administered to a patient will vary between fairly wide ranges depending upon the mode of administration, the formulation used, and the response desired.

Nasal or Intrapulmonary Administration.

By "nasal administration" is meant any form of intranasal administration of any of the peptides of this invention. The peptides may be in an aqueous solution, such as a solution including saline, citrate or other common excipients or preservatives. The peptides may also be in a dry or powder formulation.

In an alternative embodiment, peptides of this invention may be administered directly into the lung. Intrapulmonary administration may be performed by means of a metered dose inhaler, a device allowing self-administration of a metered bolus of a peptide of this invention when actuated by a patient during inspiration.

The peptides of this invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the peptide may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the peptide may be in a dried and particulate form. In a preferred embodiment, the particles are between about 0.5 and 6.0 μm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With microparticles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 μm. One type of dry powder inhaler in current use is Glaxo's Rotahaler™, which dispenses a unit dose of powder into a tube, and employs patient suction for inhalation of the powder. Other, more advanced and preferred dry powder inhalers have been or are in development, which include propellants and the like.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

In one preferred embodiment, a dry powder inhaler is employed which includes a piezoelectric crystal that deaggregates a dry powder dose, creating a small powder "cloud." Once the powder cloud is generated, an electricostatically charged plated above the powder cloud lifts the drug into the air stream. The user with one relatively easy breath can then inhale the powder. The device may be breath activated, utilizing a flow sensor that activates the electronic components upon the start of inhalation, and thereby eliminating the need for coordination of activation and breathing rhythms by the user.

Induction of Penile Response.

Both Compound 1 and Melanotan-II induce penile erections in experimental rat models when administered by intravenous routes and by other routes, including nasal administration. However, Compound 1 is approximately 100-fold more potent than Melanotan-II for inducing penile erection in the rat model. In intravenous dosing studies, penile erection was induced by Compound 1 in a broad range of concentrations, from 0.5 μg/kg of body weight to 25 μg/kg of body weight. At intravenous doses of 2 μg/kg of body weight, Compound 1 resulted in penile erection in 100% of rats tested, with approximately 50% of the rats having multiple erections during a 30 minutes observation period. By comparison, the optimal efficacious dose intravenously of Melanotan-II in the same rat model was 100 μg/kg of body weight.

The therapeutic window (the range from the desired therapeutic effect to observed adverse effects) for Compound 1 is on the order of >1,000-fold, compared to a 3- to 4-fold therapeutic window for Melanotan-II. That is, the optimal efficacious dose of Melanotan-II is approximately one-third to one-fourth the dose that causes observed adverse effects. For Compound 1, the optimal efficacious dose is less than one-one thousandth the dose that causes observed adverse effects. The significantly greater therapeutic window for Compound 1 demonstrates that it is better tolerated than Melanontan-II.

The potency of Compound 1 is significantly higher than that of Melanotan-II, meaning that significantly less Compound 1 is required for a desired effect, as compared to Melanotan-II. For example, 2 μg/kg of body weight of Compound 1 resulted in penile response by intravenous injection in rats, while 100 μg/kg of body weight of Melanotan-II was required for an equivalent penile response. The significantly higher potency results in less product being required. It further permits utilization of alternative delivery routes, including dermal, nasal and similar delivery routes, wherein higher quantities of drug may be required in order to achieve the desired effect. For example, intranasal routes of administration typically have a bioavailability substantially less than that achieved with intravenous dosing, and thus more drug must be administered by intranasal routes in order to achieve the equivalent pharmacological response.

Significant commercial advantage for Compound 1 is demonstrated by the reduced effective dose, compared to Melanotan-II, as a treatment or diagnostic for erectile dysfunction. Among the potential commercial advantages of Compound 1 are improved effectiveness; lower costs of the product; improved convenience, particularly in that the lower dose permits non-conventional delivery methods that are not feasible with Melanotan-II doses; and improved safety with a decreased risk of side-effects.

INDUSTRIAL APPLICABILITY

The invention is further illustrated by the following non-limiting examples.

EXAMPLE 1

Peptide Synthesis

The peptide Ac-Nle-cyclo(-Asp-His-D-Phe-Arg-Trp-Lys)-OH was synthesized by standard solid phase peptide synthesis methods, and is a cyclic heptapeptide melanocortin peptide analog with a free acid at the carboxyl terminus and an acetylated amino group at the amino terminus, with the structure:

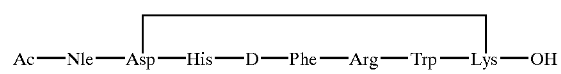

The peptide has a net molecular weight of 1025.18, and is supplied in an acetate salt form. The peptide is a white, odorless amorphous hygroscopic powder, soluble in 0.9% saline, composed of $C_{50}H_{68}N_{14}O_{10}$. For synthesis, an Fmoc-Lys($R^3$)-p-alkoxybenzyl alcohol resin was transferred to a solid phase peptide synthesizer reactor with a mechanical stirrer. The $R^3$ group, such as 1-(1'-adamantyl)-1-methylethoxycarbonyl (Adpoc), allyloxycarbonyl (Aloc) or 4-methyltrityl (Mtt), was removed and the next Fmoc-protected amino acid (Fmoc-Trp(Boc)-OH) was added to the resin through standard coupling procedures. The Fmoc protective group was removed and the remaining amino acids added individually in the correct sequence, by repeating coupling and deprotection procedures until the amino acid sequence was completed. After completion of coupling with the last Fmoc-amino acid derivative, Fmoc-Nle-OH, and cleavage of the Fmoc protective group, the exposed terminal amino group was acetylated with acetic anhydride and pyridine in N,N-dimethylformamide (DMF). The peptide-resin was dried and the Lys and Asp protective groups cleaved. The Lys and Asp deprotected peptide resin was suspended in a suitable solvent, such as DMF, dichloromethane (DCM) or 1-methyl-2-pyrrolidone (NMP), a suitable cyclic coupling reagent, such as 2-(1H-benzotriazol-1-yl)-1,1,3,3-tetramethyluronium tetrafluoroborate (TBTU), 2-(7-aza-1H-benzotriazol-1-yl)-1,1,3,3-tetramethyluronium tetrafluoroborate (TATU), 2-(2-oxo-1(2H)-pyridyl)-1,1,3,3- tetramethyluronium tetrafluoroborate (TBTU) or N,N'-dicyclohexylcarbodiimide/1-hydroxybenzotriazole (DCCl/HOBt) was added, and coupling initiated by use of a suitable base, such as N,N-diispropylethylamine (DIPEA), sym-collidine or N-methylmorpholine (NMM). After cyclization, the peptide-resin was washed and the peptide cleaved from the resin and any remaining protective groups using trifluoroacetic acid (TFA) in the presence of water and 1,2-ethanedithiol (EDT). The final product was precipitated by adding cold ether and collected by filtration. Final purification was by reversed phase HPLC using a $C_{18}$ column. The purified peptide was converted to acetate salt by passage through an ion-exchange column.

EXAMPLE 2

Binding of Compound 1 and Melanotan-II to Melanocortin Receptors

The binding of Compound 1, made as in Example 1 above, to selected melanocortin receptors was compared to binding of Melanotan-II. Melanotan-II was also made by conventional peptide synthesis, as generally described in Example 1 above.

Relative binding was determined by competitive inhibition using α-MSH. B16-F1 mouse melanoma cells were used as the source of MC1 receptors; HEK 293 cells, transfected with human melanocortin receptor sequences, were used as the source of MC3, MC4 and MC5 receptors; and Y1 cells were used as the source of MC2 receptors. A standard competitive binding assay protocol was following, using $^{125}$I-NDP-MSH as the radioligand.

Utilizing the assay procedure, the following relative binding was determined:

TABLE 1

RELATIVE BINDING $_{(Ki)}$

| COMPOUND | MC1-R (nM) | MC2-R | MC3-R (nM) | MC4-R (nM) | MC5-R (nM) |
|---|---|---|---|---|---|
| Compound 1 | 0.68 | >10$^{-6}$M | 72.07 | 19.25 | 166.8 |
| Melanotan-II | 0.12 | >10$^{-6}$M | 23.7 | 1.03 | 69.48 |

EXAMPLE 3

Agonist Activity of Compound 1

The agonist activity of Compound 1, made as in Example 1 above, was evaluated by cyclic adenosine 3':5'-cyclic monophosphate (cAMP) detection using a commercially available cAMP kit (R&D Systems, DE0350, low pH). HEK 293 cells, stably transfected with human MC4-R, were used. Compound 1 was evaluated by addition of each to cells both with and without concomitant addition of α-MSH, with α-MSH also used as a positive control. Following incubation, the medium was aspirated and cell layers extracted. The total cAMP accumulation in fixed quantities of cell extract was determined by competitive immunoassay using the cAMP kit. These results are shown on Table 2.

TABLE 2 cAMP CONCENTRATION (pMol/mL)

| Concentration of Test Compound | Compound 1 | Compound 1 + 100 nM α-MSH | α-MSH | Blank (DMEM) |
|---|---|---|---|---|
| 1 × 10$^{-7}$M | 270.2 | 180.9 | 107.7 | 8.24 |
| 2.5 × 10$^{-8}$M | 85.1 | 218.5 | 146.3 | 1.9 |

TABLE 2-continued cAMP CONCENTRATION (pMol/mL)

| Concentration of Test Compound | Compound 1 | Compound 1 + 100 nM α-MSH | α-MSH | Blank (DMEM) |
|---|---|---|---|---|
| 6.25 × 10$^{-9}$M | 115.6 | 62.6 | 45.0 | 6.5 |
| 1.56 × 10$^{-9}$M | 17.9 | 245.8 | 107.7 | 0.7 |
| 3.91 × 10$^{-10}$M | 22.7 | 127.0 | 20.2 | 2.6 |
| 0.98 × 10$^{-10}$M | 5.8 | 251.8 | 40.0 | 0.5 |

These results demonstrate that Compound 1 exhibits agonist activity to MC4-R.

EXAMPLE 4

Induction of Penile Erections Using Compound 1 and Melanotan-II

The efficacious dose of Compound 1, made as in Example 1 above, to induce penile erection in Sprague Dawley rats by intravenous dosing was determined. In the rat model of penile erection, the optimal efficacious dose by intravenous administration is 100 μg/kg body weight. Melanotan-II was also made by conventional peptide synthesis, as generally described in Example 1 above. Male Sprague Dawley rats were administered Compound 1, in the indicated dose, Melanotan-II, or a saline negative control, and were observed for erections and side effects, including excessive grooming, yawning, vacuous chewing, hypoactivity, and heaving. It is known that Melanotan-II induces these side effects as doses as low as 300 μg/kg body weight. Table 3 sets forth the results obtained:

TABLE 3

INDUCED PENILE ERECTION IN SPRAGUE DAWLEY RATS BY INTRAVENOUS INJECTION

| Drug Administered | Dose (μg/kg) | % Rats with Penile Erection | Number of Erections/Rat/ 30 Minutes |
|---|---|---|---|
| Compound 1 | 0.5 | 50% | 0.5 |
| Compound 1 | 0.75 | 50% | 0.5 |
| Compound 1 | 1.0 | 100% | 1.0 |
| Compound 1 | 2.0 | 100% | 2.0 |
| Compound 1 | 5.0 | 100% | 1.8 |
| Compound 1 | 10.0 | 100% | 2.5 |
| Compound 1 | 25.0 | 50% | 0.5 |
| Melanotan-II | 10.0 | 17% | 0.3 |
| Melanotan-II | 100.0 | 75% | 1.0 |
| Saline (Negative Control) | N/A | 0% | 0 |

Two to four rats were observed in each group, with observation over a one-half hour period following administration. No adverse side effects were observed in any rat administered Compound 1. In this and comparable experiments, it was observed that Compound 1 was efficacious at doses as low as 1 μg/kg of body weight when administered by intravenous injection, with efficacy determined by induction of penile erection in 100% of animals administered Compound 1. The comparable efficacious dose of Melanotan-II, with efficacy also determined by induction of penile erection in 100% of animals, was at least approximately 100 μg/kg body weight. This resulted in the unexpected conclusion that Compound 1 was at least approximately 50-fold more potent for inducing erection in a rat model when administered by intravenous injection than is Melanotan-II. In other studies, no adverse side effects, including excessive grooming, yawning, vacuous chewing, hypoactivity, or heaving, were observed on administration of intravenous doses of Compound 1 as high as 3,000 μg/kg body weight.

EXAMPLE 5
Pharmacokinetics in Rats Following IV Administration of Compound 1

A sensitive bioassay, based on high affinity binding to MCRs, was used to monitor plasma levels of Compound 1 in dosed rats. Rats were dosed intravenously with 100 μg/kg of Compound 1. A bi-phasic pharmacokinetic profile resulted, as shown in FIG. 1.

EXAMPLE 6
Pre-formulation Studies for Nasal Delivery

A series of pre-formulation studies for nasal delivery were conducted. This study shows the stability of the peptide Ac-Nle-cyclo(-Asp-His-D-Phe-Arg-Trp-Lys)-OH, at a concentration of 0.825 mg/mL, over a period of twelve weeks, with storage at 40° C.

EXAMPLE 7
Formulations for Nasal Delivery

Based on the pre-formulation study of Example 6, two formulations were prepared. For the first, the peptide Ac-Nle-cyclo(-Asp-His-D-Phe-Arg-Trp-Lys)-OH was dissolved in a 0.9% saline solution, pH approximately 6.0, at a concentration of 0.825 mg per mL of solution (Nasal Formulation 1).

EXAMPLE 8
Inhibition of Compound 1 Using Melanocortin Antagonist

Figure 4:
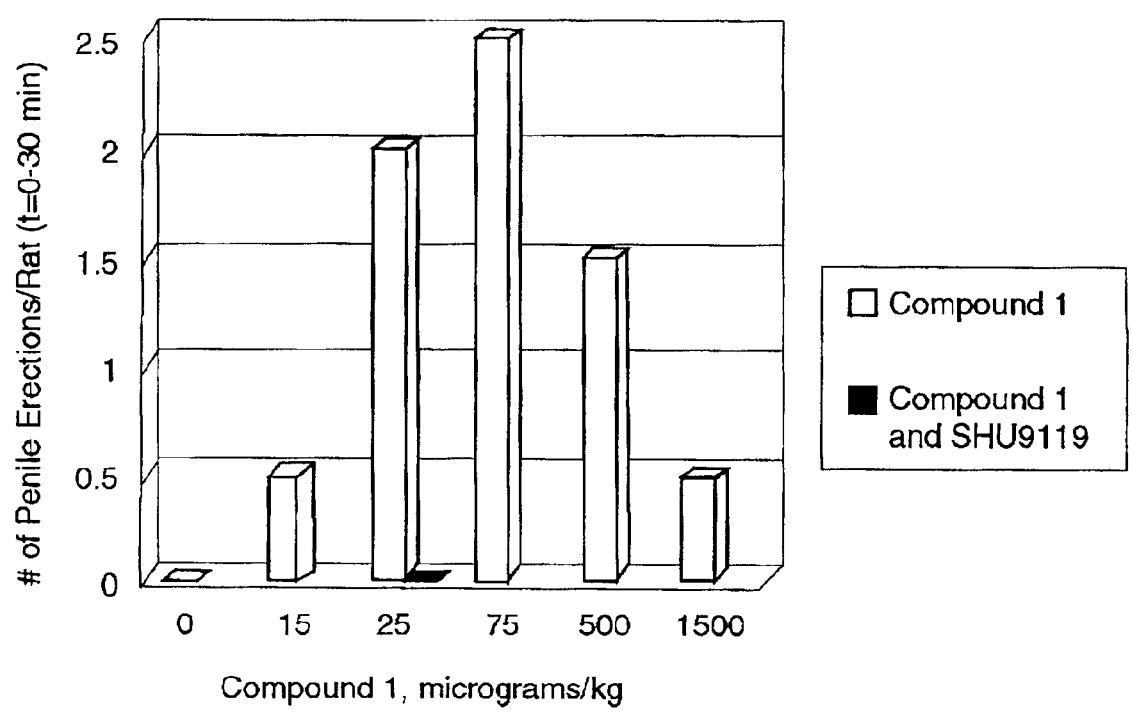
FIG. 4 is a plot of the intranasal efficacy in rats of different amounts of Compound 1.

The effect of a nonselective melanocortin antagonist, SHU9119 (Hruby V J, Lu D, Sharma S D, et al. *J Med Chem* 38:3454–3461 (1995)), Ac-Nle-cyclo(-Asp-His-D-Nal(2')-Arg-Trp-Lys)-NH$_2$, to inhibit induction of penile erection with Compound 1 was studied. A group of four Sprague Dawley rats were administered 5 μg/kg of SHU9119 by intravenous administration, and five minutes later 25 or 50 μg/kg of Compound 1 in Nasal Formulation 1 was administered by nasal administration. No erections were observed in the rats over the one-half hour observation period. No erections were observed in rats administered a saline control by nasal administration. In control groups, 100% of the rats administered the same dose of Compound 1 by the same route of administration, but without pre-administration of SHU9119, had observed erections. FIG. 4 shows the number of penile erections per rat during the initial 30 minute period post-administration; as shown for the 25 μg/kg level, no penile erections were observed with pre-administration of SHU9119.

EXAMPLE 9
Nasal Administration to Cynomolgus Monkeys

Nasal Formulation 1 of Example 6 was administered to cynomolgus monkeys by nasal spray, at a dose of approximately 50 μg per kg of body weight. Compared to intravenous injection of the same dose of Ac-Nle-cyclo(-Asp-His-D-Phe-Arg-Trp-Lys)-OH, the mean bioavailability of the peptide using Nasal Formulation 1 was approximately 0.73%±0.05. In a related cardiovascular safety study using cynomolgus monkeys with intranasal administration of Nasal Formulation 1, an erection lasting approximately one hour was observed in one of four monkeys.

Figure 2:
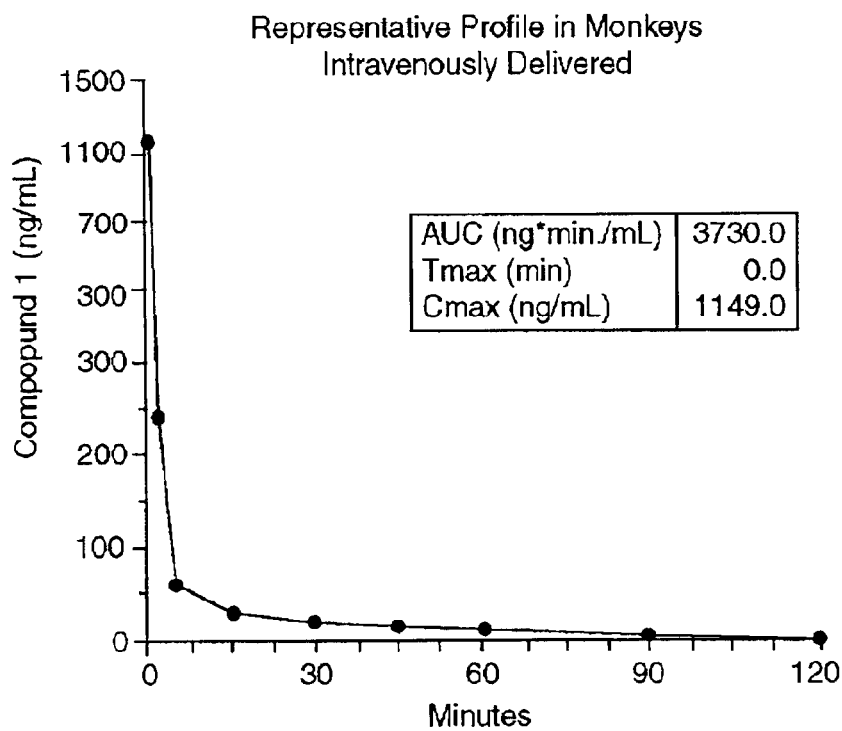
FIG. 2 is a plot of the pharmacokinetic profile in monkeys intravenously administered 50 μg/kg body weight of Compound 1.
Figure 3:
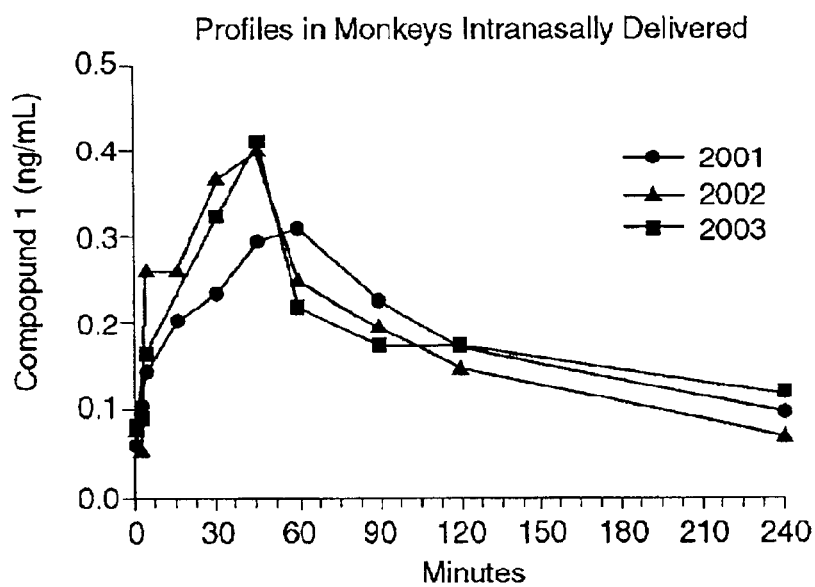
FIG. 3 is a plot of the pharmacokinetic profile in a monkey intranasally administered 50 μg/kg body weight of Compound 1.

EXAMPLE 10
Pharmacokinetic Profiles Following Administration to Cynomolgus Monkeys A sensitive radioimmunoassay was used to monitor plasma levels of Compound 1 in cynomolgus monkeys. Monkeys were dosed intravenously with 50 μg/kg of Compound 1. A bi-phasic pharmacokinetic profile resulted, as shown in FIG. 2. Selected monkeys were intranasally administered 50 μg/kg of Compound 1 in Nasal Formulation 1, and the resulting pharmacokinetic profiles are shown in FIG. 3.

EXAMPLE 11
Nasal Administration Dosing Study in Rats

In another series of experiments, a dosing study was conducted in rats by nasal administration of from 15 μg per kg of body weight to 1500 μg per kg of body weight, using Nasal Formulation 1. Based on penile erectile response behavior, the peptide was efficacious at all dose amounts administered, and particularly from 25 μg/kg to 75 μg/kg, with pharacologic effect observed over the range from 15 μg/kg to 1500 μg/kg. In addition, the response rate and side effects differed significantly from those demonstrated with nasal administration of Melanotan-II. With nasal administration of the peptide of Melanotan-II, the penile erection response was primarily in the $2^{nd}$ and $3^{rd}$ ten-minute period, while with Nasal Formulation 1 the penile erection response was primarily in the $1^{st}$ and $2^{nd}$ ten-minute period. Additionally, no adverse side effects were detected at any dosage level with Nasal Formulation 1, while adverse side effects were seen with administration of higher doses of the peptide of Melanotan-II. Table 4 sets forth the comparative data:

TABLE 4

INDUCED PENILE ERECTION IN SPRAGUE DAWLEY RATS BY INTRANASAL ADMINISTRATION

| Drug Administered | Dose (μg/kg) | % Rats with Penile Erection | Number of Erections/Rat/ 30 Minutes |
|---|---|---|---|
| Compound 1 | 15 | 50% | 0.5 |
| Compound 1 | 25 | 100% | 2.0 |
| Compound 1 | 37 | 100% | 2.0 |
| Compound 1 | 50 | 100% | 2.0 |
| Compound 1 | 75 | 100% | 2.5 |
| Compound 1 | 500 | 100% | 1.5 |
| Compound 1 | 1000 | 100% | 1.5 |
| Compound 1 | 1500 | 50% | 0.5 |
| Melanotan-II | 100 | 25% | 0.25 |
| Melanotan-II | 500 | 100% | 1.0 |
| Saline (Negative Control) | N/A | 0% | 0 |

EXAMPLE 12
Pharmacokinetic Profiles Following Administration to Beagle Dogs

Figure 5:
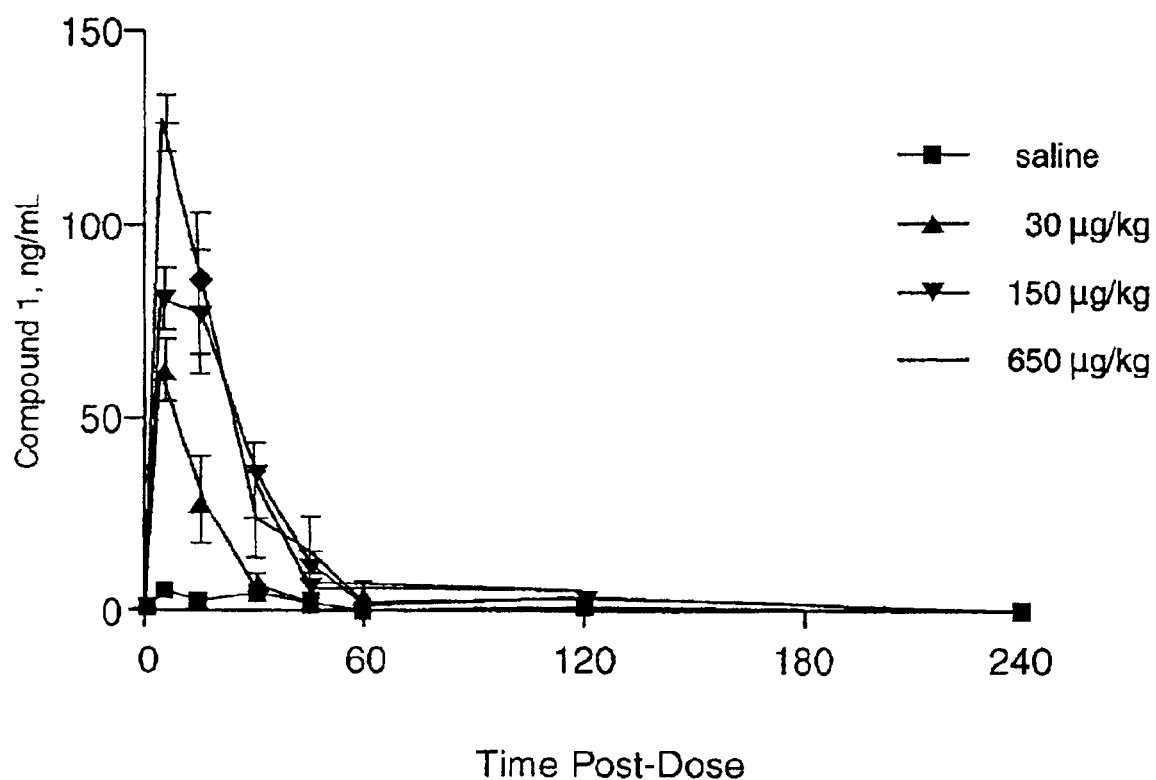
FIG. 5 is a plot of pharmacokinetic profile in Beagle dogs intranasally administered 30, 150 and 650 μg/kg body weight of Compound 1.

A sensitive bioassay, based on high affinity binding to melanocortin receptors, was used to monitor plasma levels of Compound 1 in Beagle dogs. The dogs were administered 0 (control), 30, 150 or 650 μg/kg of Compound 1 in Nasal Formulation 1 by nasal administration. The pharmacokinetic profile through four hours post-administration is shown in FIG. 5.

EXAMPLE 13
Female Sexual Response in Rats

Figure 6:
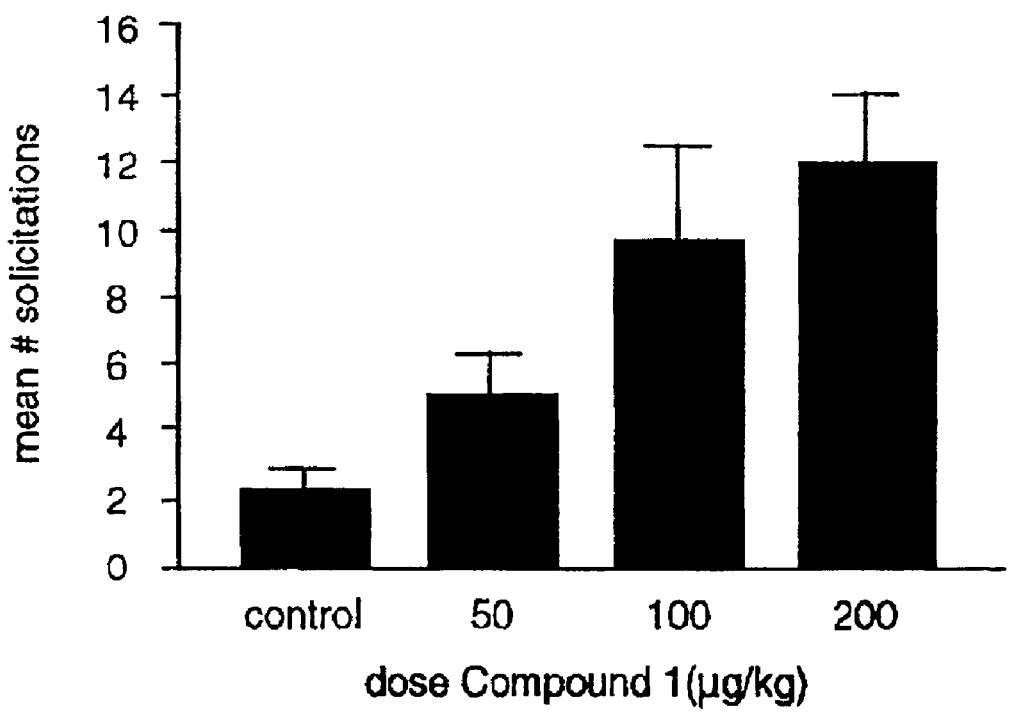
FIG. 6 is a graph of solicitations in fully primed (estrogen and progesterone) female rats following administration of 0, 50, 100 and 200 μg/kg body weight of Compound 1.
Figure 7:
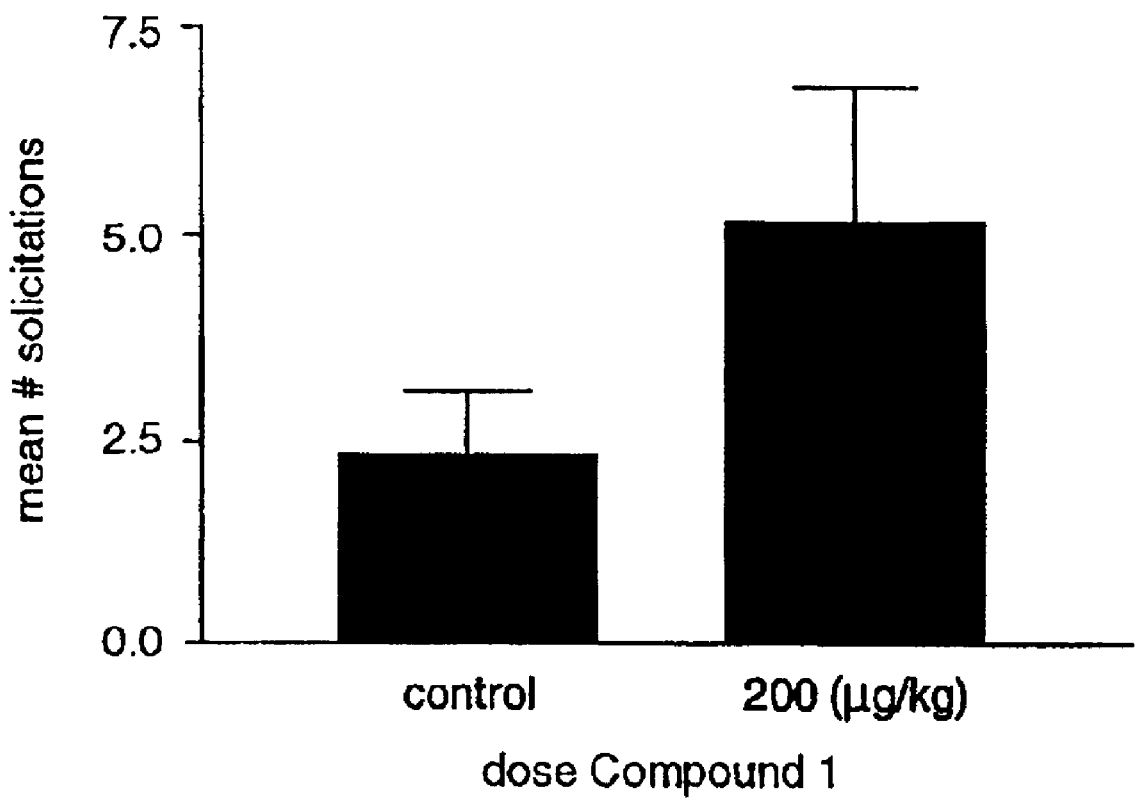
FIG. 7 is a graph of solicitations in partially primed (estrogen alone) female rats following administration of 0 and 200 μg/kg body weight of Compound 1.
Figure 8A:
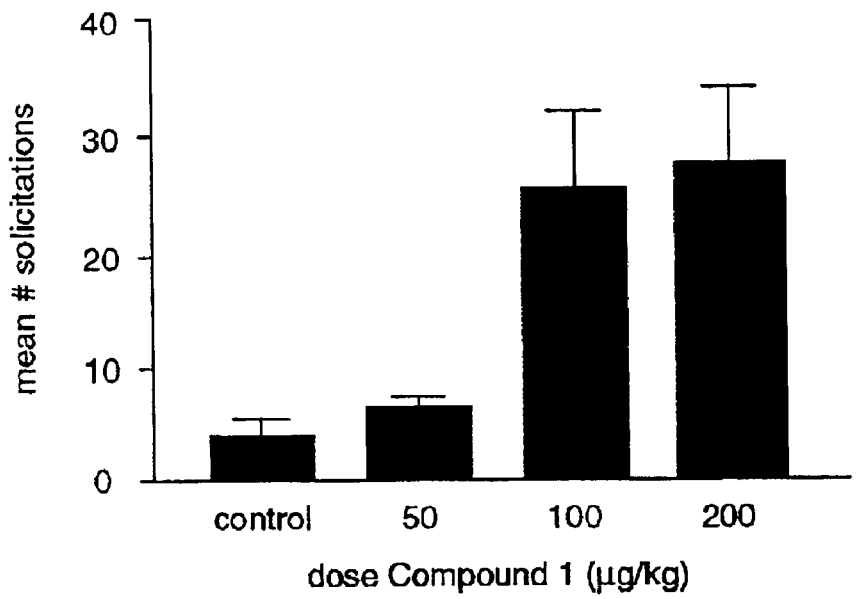
FIG. 8A is a graph of solicitations in fully primed female rats following administration of 0, 50, 100 and 200 μg/kg body weight of Compound 1, where ANOVA P<0.001 for the experiment.
Figure 8B:
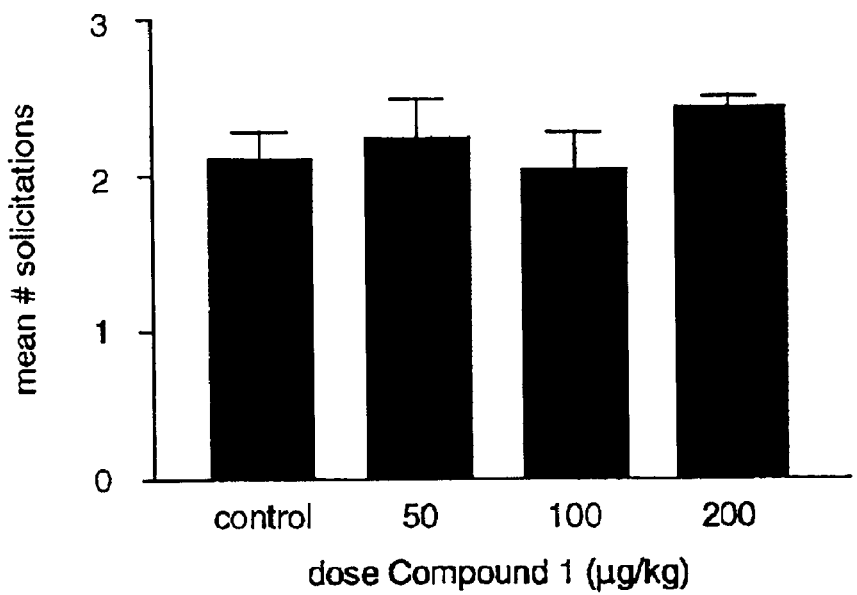
FIG. 8B is a graph of lordosis magnitude in fully primed female rats following administration of 0, 50, 100 and 200 μg/kg body weight of Compound 1.
Figure 8C:
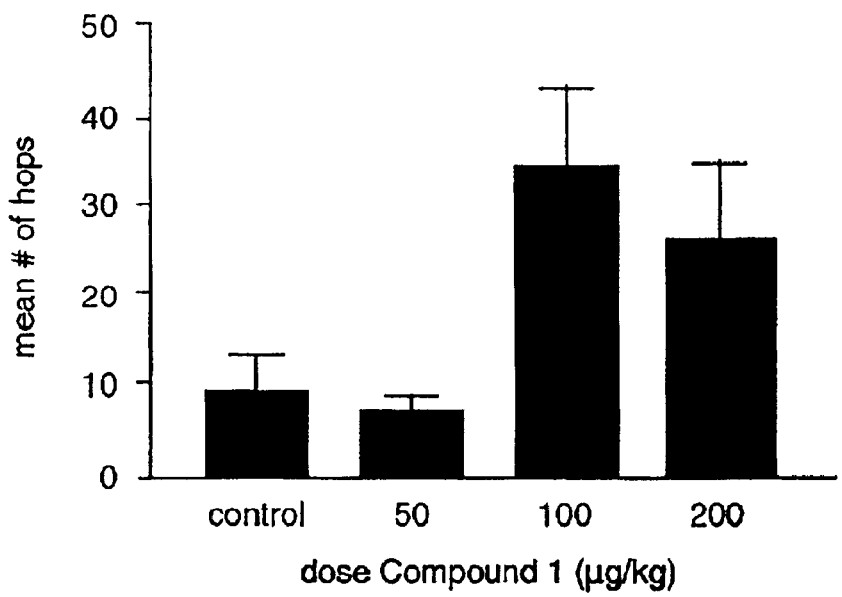
FIG. 8C is a graph of hops and darts in fully primed female rats following administration of 0, 50, 100 and 200 μg/kg body weight of Compound 1, where ANOVA P<0.02 for the experiment.
Figure 8D:
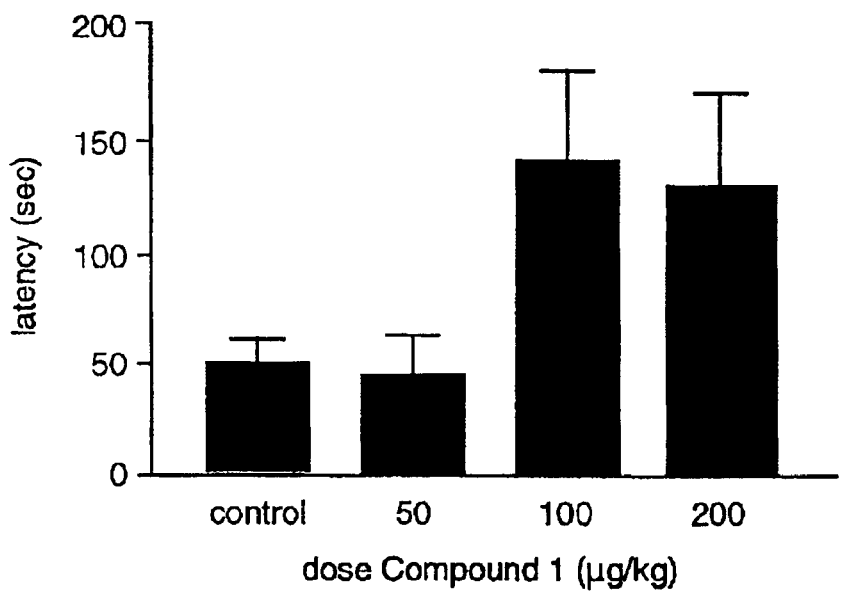
FIG. 8D is a graph of return latency, in seconds, after ejaculation in fully primed female rats following administration of 0, 50, 100 and 200 μg/kg body weight of Compound 1, where ANOVA P<0.02 for the experiment.

Female Long-Evans rats (200–250 g) were house in groups of 2 to 4 depending on size in plastic cages in a colony room maintained on a reversed 12:12 hour light/dark cycle at approximately 21° C. with food and water ad libitum. The rats were ovariectomized bilaterally via lumbar incisions one week prior to preliminary tests of sexual behavior. Intact Long-Evans male rats served as stimulus males, and were sexual vigorous, initiating copulatory activity with females within 15 seconds of being placed into bilevel chambers containing female rats. Following preliminary tests of sexual behavior, females were administered subcutaneous injections of estradiol benzoate, 10 µg in 0.1 mL of sesame oil, forty-eight hours prior to testing, and progesterone, 500 µg in 0.1 mL of sesame oil, four hours prior to testing. Administration of estradiol benzoate and progesterone induced full sexual receptivity in the female rats. Female rats were placed in bilevel chambers five minutes prior to the introduction of a sexual vigorous male. After females acquired baseline rates of sexual activity, a dose response analysis of Compound 1 was conducted, with 0, 50, 100 or 200 µg/kg, injected subcutaneously, one minute before each test. Tests were videotaped and score subsequently for appetitive level changing during the five minute period prior to the introduction of the male, lordosis quotients and reflex magnitudes, incidents of solicitation (headwise orientation and runaway), hops and darts, pacing (level changes per mount), female mounts and defensive responses. FIG. 6 depicts results, with a between-subjects analysis of variance (ANOVA) of P<0.004. In a second experiment, female rats were administered only estradiol benzoate prior to administration of 0 or 200 µg/kg of Compound 1 injected subcutaneously. The results are shown in FIG. 7. In general, in both experiments the 200 µg/kg dose of Compound 1 increased the number of solicitations significantly without affecting rates of appetitive level changing, pacing, lordosis, female mounts or rejection responses.

EXAMPLE 14
Female Sexual Response in Rats

Female Long-Evans rats as in Example 13 were tested in a unilevel pacing chambers bisected by a four-holed divider, as generally described in Yang L. V. and Clemens L. G., *Physiol Behav* 61:889–894 (1997), for five minutes prior to the introduction of a sexually vigorous male for a thirty-minute test of copulation. As in Example 13, following priming with estradiol benzoate and progesterone, 0, 50, 100 or 200 µg/kg of Compound 1 was administered subcutaneously one minute before each test, with female animals placed in the unilevel pacing chambers bisected by the four-hole divider through which only the females could pass. Tests were videotaped and scored as in Example 13, with pacing defined as number of exits from and returns to the side with the male; and exist and return latencies following mounts, intromissions or ejaculations. FIGS. 8A, 8B, 8C and 8D show the results. The 200 µg/kg dose of Compound 1 increased the number of solicitations, hops and darts, and female mounts significantly compared to controls, but had no effect on lordosis or defensive responding. This dose also increase the ejaculation return latencies, but not the mount or intromission return latencies. This dose had no significant effect on the number of exits or returns made by the females.

EXAMPLE 15
Ferret Emesis Study

Groups of six ferrets were studied for emetic effect of Compound 1 and Melanotan-II at various dose ranges with delivery both by intravenous and intranasal administration. Ferrets are a recognized model for emetic studies. The vehicle for both intravenous and intranasal administration was saline. The positive control was cisplatin, known to induce vomiting in ferrets. The data is described as the number of animals out of a group of six showing signs of vomiting.

TABLE 5

EMETIC EFFECT COMPARISON

| Dosages in µg/kg Intravenous (IV) | Signs of vomiting (proportions) | |
| --- | --- | --- |
| Intranasal (IN) | Compound 1 | Melanotan-II |
| Vehicle (saline) | 0/6 | 0/6 |
| 10 (IV) | 0/6 | 1/6 |
| 30 (IV) | 6/6 | 4/6 |
| 100 (IV) | 6/6 | 6/6 |
| 100 (IN) | 0/6 | 0/6 |
| 300 (IN) | 1/6 | 5/6 |
| 500 (IN) | 1/6 | 6/6 |

EXAMPLE 16

Administration for Treatment of Male Erectile Dysfunction

For treatment of male erectile dysfunction in human males with psychogenic erectile dysfunction, a dose of Compound 1 in a nasal formulation is administered by means of a nasal administration metered dose device. The device dispenses a metered volume, such as a 100 µL spray volume, and is optionally administered by the patient into a single nostril. If desired, erectile response is measured using an appropriate device, such as a Rigiscan (Dacomed).

EXAMPLE 17

Administration for Treatment of Female Sexual Dysfunction

For treatment of female sexual dysfunction in human females with psychogenic sexual dysfunction, a dose of Compound 1 in a nasal formulation is administered by means of a nasal administration metered dose device. The device dispenses a metered volume, such as a 100 µL spray volume, and is optionally administered by the patient into a single nostril.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A pharmaceutical composition, comprising a peptide in a pharmaceutically acceptable aqueous carrier, wherein said peptide is a free acid or a pharmaceutically acceptable salt thereof comprising the sequence Nle-cyclo(-Arg-His-D-Phe-Arg-Trp-Lys)-OH.

2. The pharamceuticai composition of claim 1, wherein said peptide is cyclicized through the side chains of Asp and Lys without introduction of an additional molecular unit.

3. The pharmaceutical composition of claim 1, wherein said peptide has an acetylated amino group at amino terminus.

4. The pharmaceutical composition of claim 1, wherein the peptide consists of the sequence Ac-Nle-cyclo(-Asp-His-D-Phe-Arg-Trp-Lys)-OH.

5. A method for stimulating sexual response in a mammal, comprising administering a pharmaceutically sufficient amount of a composition comprising a peptide or pharmaceutically acceptable salt thereof of the formula Ac-Nle-cyclo(-Asp-His-D-Phe-Arg-Trp-Lys)-OH for a time and under conditions effective to stimulate a sexual response.

6. The method of claim 5, wherein the mammal is a male.

7. The method of claim 5, wherein the mammal is a female.

8. The method of claim 5, wherein the pharmaceutically sufficient amount is at a dose level that does not induce emesis or other deleterious side effects.

9. The method of claim of claim 5, wherein the composition further comprises a pharmaceutically acceptable carrier.

10. The method of claim 5, wherein administering comprises a method of administration selected from the group consisting of administration by injection, administration through mucous membranes, buccal administration, oral administration, dermal administration, inhalation administration and nasal administration.

11. The method of claim 10, wherein administering comprises nasal administration of a metered amount of a formulation comprising an aqueous buffer.

12. The method of claim 11, wherein the aqueous buffer is a member selected from the group consisting of saline and citrate buffer.

13. A purified peptide or pharmaceutically acceptable salt thereof consisting of Ac-Nle-cyclo(Asp-His-D-Phe-Arg-Trp-Lys)-OH.

14. An isolated peptide or pharmaceutically acceptable salt thereof consisting of Ac-Nle-cyclo(-Asp-His-D-Phe-Arg-Trp-Lys)-OH.

15. A pharmaceutical kit, comprising the pharmaceutical composition of claim 1 disposed in a nasal administration device.

16. The pharmaceutical kit of claim 15 wherein the nasal administration device is a metered dose nasal administration device.

17. The pharmaceutical kit of claim 16 wherein the metered dose nasal administration device dispenses a metered spray volume of approximately 100 μL.

18. The pharmaceutical kit of claim 15 wherein the pharmaceutically acceptable salt is an acetate salt.

* * * * *

UNITED STATES PATENT AND TRADEMARK OFFICE
CERTIFICATE OF CORRECTION

PATENT NO. : 6,794,489 B2   Page 1 of 1
APPLICATION NO. : 10/040547
DATED : September 21, 2004
INVENTOR(S) : Christine H. Blood et al.

It is certified that error appears in the above-identified patent and that said Letters Patent is hereby corrected as shown below:

In the Claims:

Column 17, Claim 1, Lines 24-25, delete the sequence "Nle-cyclo(-Arg-His-D-Phe-Arg-Trp-Lys)-OH" and replace with "Nle-cyclo(-Asp-His-D-Phe-Arg-Trp-Lys)-OH".

Signed and Sealed this
Fourteenth Day of May, 2013

Teresa Stanek Rea
*Acting Director of the United States Patent and Trademark Office*

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial
      Sequence:alpha-melanocyte-stimulation hormone
      tetrapeptide core sequence

<400> SEQUENCE: 1

His Phe Arg Trp
  1
```